United States Patent [19]

Irwin et al.

[11] 4,007,638
[45] Feb. 15, 1977

[54] LIQUID SAMPLING

[75] Inventors: Malcolm F. Irwin, West Chester; Charles A. McClure, Malvern, both of Pa.

[73] Assignee: Pro-Tech Inc., Malvern, Pa.

[22] Filed: Sept. 29, 1975

[21] Appl. No.: 617,649

[52] U.S. Cl. .............................. 73/421 A; 73/423 A
[51] Int. Cl.² ......................................... G01N 1/18
[58] Field of Search ......... 73/421 R, 421 A, 421 B, 73/423 R, 424, 423 A

[56] References Cited
UNITED STATES PATENTS

| | | | |
|---|---|---|---|
| 2,625,952 | 1/1953 | Eide et al. | 73/421 A X |
| 3,509,770 | 5/1970 | Morton | 73/423 R X |
| 3,561,273 | 2/1971 | Tanila | 73/423 R |
| 3,583,235 | 6/1971 | Tanila | 73/423 R |
| 3,751,990 | 8/1973 | Blechman | 73/423 R |
| 3,788,145 | 1/1974 | Irwin | 73/421 B |
| 3,848,633 | 11/1974 | Hurtig et al. | 73/423 A X |

*Primary Examiner*—Richard C. Queisser
*Assistant Examiner*—Joseph W. Roskos
*Attorney, Agent, or Firm*—Charles A. McClure

[57] ABSTRACT

Liquid samples of like composition and like or unlike volume are collected simultaneously. Liquid is withdrawn continuously from a body of liquid to be sampled. The withdrawn liquid is passed continuously into and fills a confining region having multiple outlets. Streams of liquid from the respective outlets are diverted intermittently for sample collection and otherwise are returned to the source body of liquid or to waste. The multiple-outlet confining region is embodied in a plenum chamber, and individual diverter chambers are provided for the streams of liquid from the plenum chamber, together with means for effecting the diversion.

12 Claims, 5 Drawing Figures

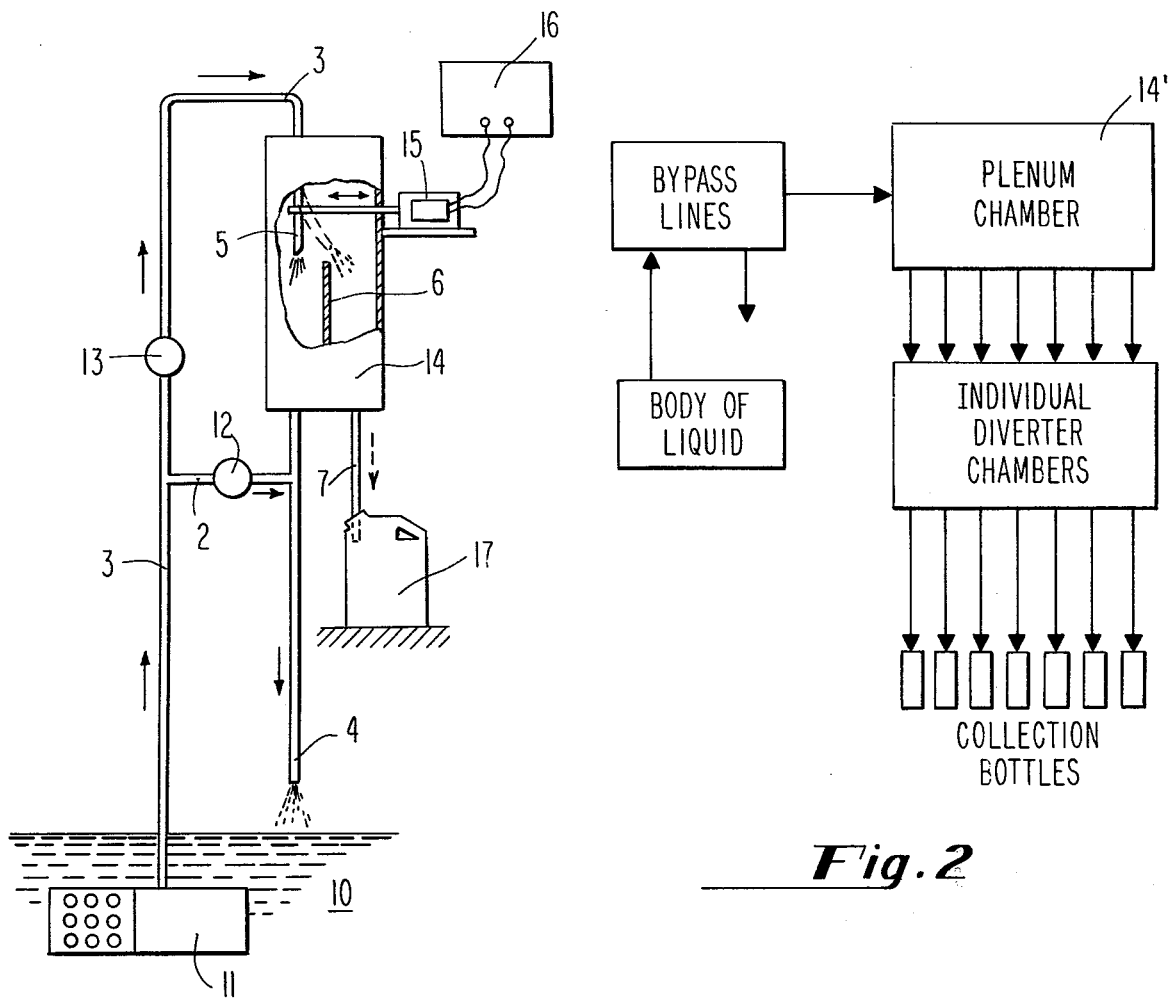
Fig. 1
Fig. 2
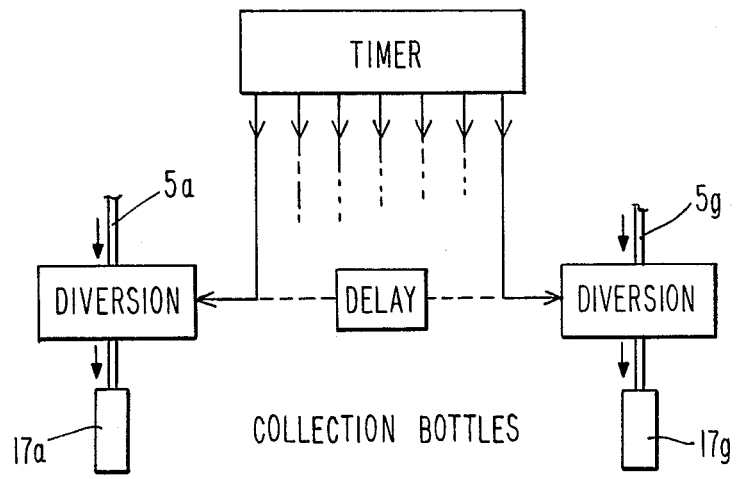
Fig. 3

LIQUID SAMPLING

This invention relates to liquid sampling, especially the sampling of liquid to provide a plurality of like samples simultaneously.

Increasing emphasis upon quality of the environment has given rise to increased sampling of liquids for determination of composition, particularly component contaminants or pollutants. Analysis for more than one component necessitates more than one sample, or at least more than one portion of the same sample. Once a sample is in a collection container, however, a portion decanted from it is very likely to differ a good deal from what is left behind in the container, and successive decanting is almost certain to provide a final fraction that is quite different from the initially decanted fraction. For this reason alone, simultaneous collection of like samples is appropriate and may be required.

Some types of pollutant change in concentration or composition (or both) in a collection bottle at ordinary temperatures and should be inhibited from changing if subsequent analysis is to reflect accurately the condition that prevailed in the liquid when it was sampled. As various inhibitors can affect one another or an inhibitor for one component may alter the concentration of another component, separate sample collection bottles are necessary to accommodate the respective inhibitors.

A primary object of the present invention is provision of a plurality of like samples simultaneously.

Another object is collection of simultaneous samples alike except for desired differences in sample volume.

A further object is provision of apparatus for accomplishing the foregoing objects.

Other objects of this invention, together with means and methods for attaining the various objects, will be apparent from the following description of a preferred embodiment of the invention, which is presented by way of example rather than limitation.

FIG. 1 is a schematic side elevation of apparatus providing background for this invention;

FIG. 2 is a block diagram of an embodiment of the present invention;

FIG. 3 is a block diagram showing timing interconnections of the invention;

Figure 4:
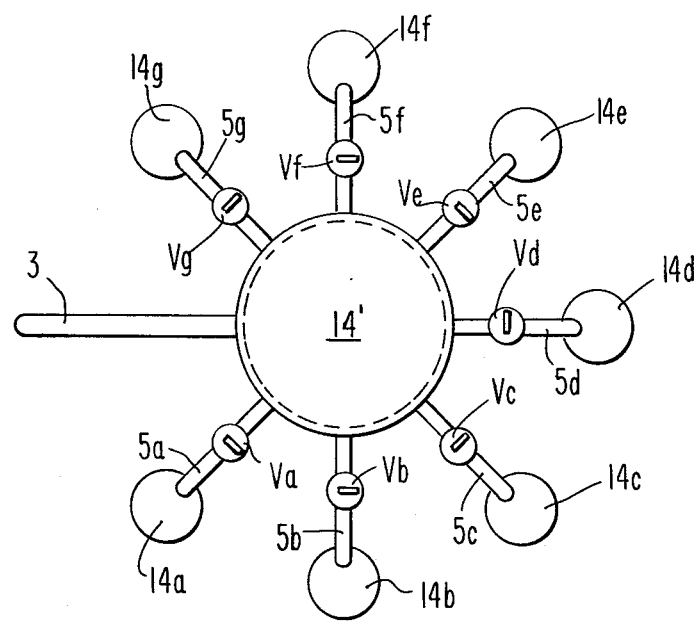
FIG. 4 is a schematic top plan of apparatus embodying the invention.

In general, the objects of the present invention are accomplished, in liquid sampling wherein liquid is withdrawn from a body of liquid being sampled to flow past an intermittent diversion locus and back to the body of liquid or to waste except when being diverted from such locus to a collection location, for the purpose of providing a plurality of separate samples simultaneously, comprising passing the flow of liquid through a first temporarily confining region having a plurality of outlets therefrom, separately flowing streams of liquid from the respective outlets into a second temporarily confining region and past loci of intermittent diversion therein and back to the body of liquid or to waste except when being diverted, intermittently diverting each such stream at its diversion locus to the collection location, and collecting them as individual samples thereat.

In apparatus terms the invention is directed to improved means for collecting multiple samples comprising a plenum chamber interposed to receive the flow from the body of liquid and having a plurality of outlets therefrom, a plurality of diversion devices to receive individual streams of liquid from the respective outlets and for diverting them intermittently into individual sample collection containers.

FIG. 1 shows a conventional flow-through type of liquid sampler in which submersible pump 11 with intake screen under the surface of body of liquid 10 has flow line 3 leading to diverter chamber 14 of the sampler. Bypass line 2 with bypass valve 12 interconnects the flow line to return or waste line 4, shown as discharging from the diverter chamber back into the body of liquid to complete the bypass path. Trim valve 13 in the portion of flow line 3 cooperates with the bypass valve in precluding an excessive flow rate into the diverter chamber.

Flexible inlet tube 5 in diverter chamber 14 normally is oriented vertically (as shown in solid lines) to discharge into a primary compartment at the left of baffle 6 rising vertically from the bottom of the chamber, whereupon the discharged liquid drains from the chamber via return or waste line 4 connected to an outlet (not separately shown) at the bottom left of the chamber. Alternatively, whenever timer 16 (or an alternative timing source) actuates solenoid 15, inlet tube 5 is flexed temporarily to the right to discharge into a secondary compartment, at the right of baffle 6, from which the discharged liquid drains via sample line 7 into sample collection bottle 17. Cessation of the timing signal deactuates the solenoid, releasing the inlet tube to its normally vertical position for discharge to waste.

FIG. 2 shows in block form the lines, here called Bypass Lines, shown in more detail in the preceding view, and Plenum Chamber 14' interconnected thereto in place of previous diverter chamber 14. The plenum chamber is shown with multiple (seven) outlets to distribution lines leading individually to a corresponding number of Individual Diverter Chambers similarly connected individually to a like number of Collection Bottles, in contrast to the single bottle shown previously.

FIG. 3 shows schematically a Timer connected to actuate Diversion of the liquid stream in the respective diverter chambers, two shown: 5a and 5g, along with their respective Collection Bottles 17a and 17g. Also provided is Delay of the diversion timing interconnectable to only part or all of the diverter chambers, as desired. It will be understood that many conventional timers are available for use as illustrated, including provision of a delayed output, adjustable from the nil upward, as well as a relatively non-delayed output. The structure of such timer does not constitute any part of this invention, and, thus, is not described further here.

Figure 5:
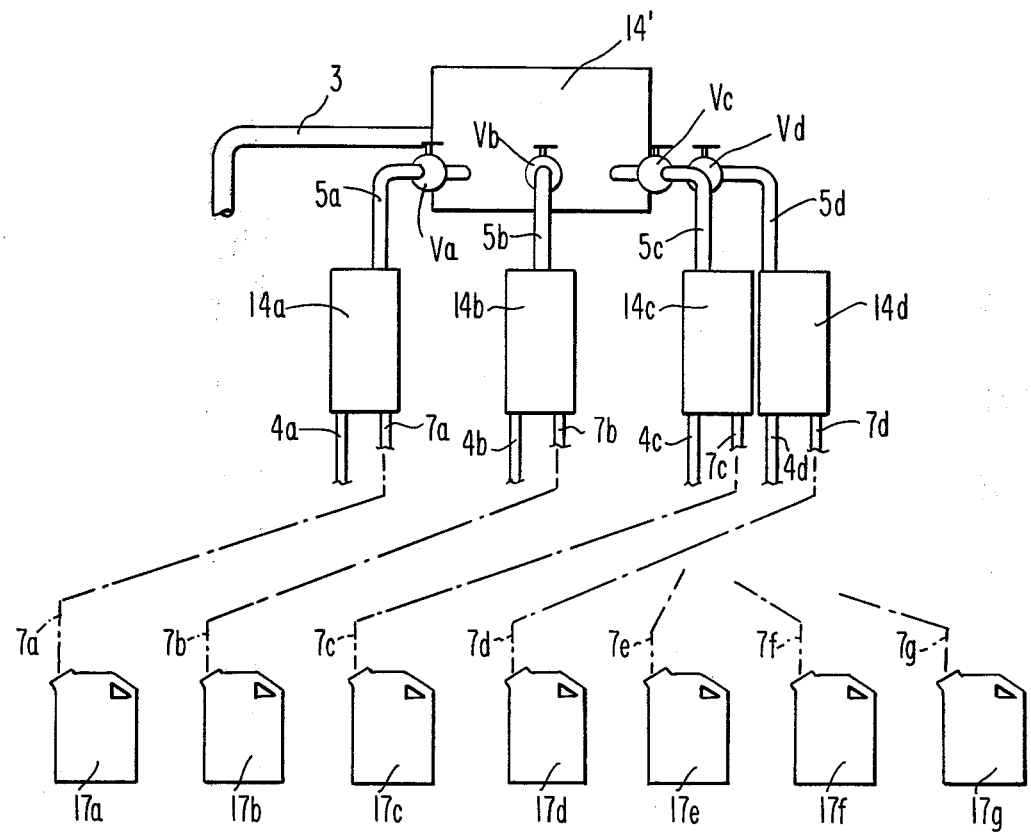
FIG. 5 is a fragmentary schematic side elevation of equipment of preceding views.

FIGS. 4 and 5 show plenum chamber 14' and individual diverter chamber 14a to 14g in more detail. Individual diversion solenoids for the respective diverter chambers, similar to solenoid 15 of FIG. 1, are omitted from this view for clarity. Distribution lines 5a to 5g are furnished with individual valves Va to Vg for regulating flow therethrough to the corresponding diverter chambers. Shown fragmentarily at the left is flow line 3 to the plenum chamber. Underneath each chamber is one of return lines 4a to 4g (only 4a to 4d being visible, in FIG. 5) and one of sample lines 7a to 7g, the latter leading to collection bottles 17a to 17g. Sample lines 7a, 7b, 7c conceal all but one of the other sample lines from view, but broken lines indicate the distribution of all sample lines to their respective collection bottles 7a to 7g, all of which are shown.

Operation of the disclosed apparatus according to this invention is readily summarized and equally readily understood. A stream of liquid is pumped from the body of liquid to be sampled through the flow line and the flexible inlet tube into the plenum chamber, from which it flows into each of the individual diverter chambers. The stream of liquid in each diverter chamber normally flows by gravity from the primary compartment therein out the return line, but the timer actuates the diverter solenoid intermittently to divert the stream momentarily into the secondary compartment of the diverter chamber, whereupon the diverted liquid flows from the secondary compartment out the individual sample line and into the corresponding bottle. Then the inlet tube solenoid is deactuated, whereupon the stream of liquid reverts to the primary compartment and out the return line. The various valves are adjustable, such as to ensure substantially equal sample volumes, as is usually desired.

Actuation of various of the diversion solenoids may be delayed to reduce the volume of the samples diverted therein relative to samples from one or more other of the diverter chambers. Unequal sample volumes also can be favored where desired by using dissimilar distribution (and sizes of sample) lines. Normally the sample obtained via the distribution line opposite flow line 3 tends to be larger than the others at similar valve settings in the absence of compensating baffles within the plenum chamber or relocation of the flow lines to enter the plenum chamber vertically at the center of the top or bottom face.

Suitable materials of construction for the apparatus of this invention are readily available, being wholly conventional and not forming any part of the invention itself. Polyvinyl chloride (PVC) is a convenient composition for the chamber and lines, which alternatively may be made of tetrafluoroethylene (TFE) or other suitable plastic, or even of stainless steel. Various parts of the apparatus may be made of different ones of these or other similarly suitable materials, of course.

Although a single embodiment of this invention has been described and illustrated, modifications may be made therein, as by adding, combining, deleting, or subdividing parts or steps, or substituting equivalents, while retaining at least some of the benefits of the invention, which itself is defined in the following claims.

We claim:

1. In liquid sampling wherein liquid is withdrawn from a body of liquid being sampled to flow past an intermittent diversion locus and back to the body of liquid or to waste except when being diverted from such locus to a collection location, the improvement in providing a plurality of separate samples simultaneously comprising passing the flow of liquid through a first temporarily confining region having a plurality of outlets therefrom, separately flowing streams of liquid from the respective outlets into a second temporarily confining region and past loci of intermittent diversion and back to the body of liquid or to waste except when being diverted, intermittently diverting each such stream at its diversion locus to the collection location, and collecting them as individual samples thereat.

2. Liquid sampling according to claim 1, including the step of regulating the relative flows from the outlets of the primary temporarily confining region.

3. Liquid sampling according to claim 1, including the step of controlling the respective periods of diversion at the individual diversion loci.

4. Liquid sampling according to claim 3, wherein a plurality of unlike periods of diversion are provided so as to collect samples of a plurality of sample volumes.

5. In apparatus for sampling liquid from a body thereof, including means for flowing liquid therefrom past an intermittent diversion locus and back to the body of liquid or to waste except when being diverted from such locus to a collection location, improved means for collecting multiple samples comprising a plenum chamber interposed to receive the flow from the body of liquid and having a plurality of outlets therefrom, a plurality of diversion devices to receive individual streams of liquid from the respective outlets and for diverting them intermittently into individual sample collection containers.

6. Liquid sampling apparatus according to claim 5, including bypass means for regulating the liquid flow into the plenum chamber by bypassing any excess back to the body of liquid or to waste.

7. Liquid sampling apparatus according to claim 5, including valve means at the plenum chamber outlets for regulating the flow of the respective streams of liquid therefrom.

8. Liquid sampling apparatus according to claim 5, including timer means for controlling the periods of diversion and, thus, the sample volume.

9. Apparatus for sampling liquid from a body thereof, including means for flowing liquid therefrom past an intermittent diversion locus and back to the body of liquid or to waste except when being diverted from such locus to a collection location, and comprising a plenum chamber interposed to receive the flow from the body of liquid and having a plurality of outlets therefrom, a plurality of diversion devices to receive individual streams of liquid from the respective outlets and for diverting them intermittently into respective temporarily confining chambers, each such chamber having an outlet to an individual sample collection container, valve means at the outlets from the plenum chamber for regulating the flow of the respective streams of liquid therefrom, and timer means for controlling the periods of diversion and, thus, the volumes of the respective samples.

10. Liquid sampling apparatus according to claim 9, wherein delay means associated with the timer means facilitates unlike diversion periods and, thus, diverse sample volumes.

11. Apparatus for providing multiple samples of liquid simultaneously from a body thereof, comprising means for withdrawing a stream of liquid therefrom, a plenum chamber interconnected to the withdrawing means to receive the stream of liquid and be filled thereby, a multiplicity of separate outlets from the plenum chamber, diversion devices interconnected to the respective outlets to receive individual streams of liquid therefrom, and means for actuating the diversion devices intermittently to divert liquid therefrom for sample collection, the diverter devices being adapted to pass the streams of liquid received thereby back to the body of liquid or to waste except when so actuated.

12. Liquid sampling apparatus according to claim 11, wherein the withdrawing means comprises a pump submersible in the body of liquid.

* * * * *